(12) United States Patent
Lee et al.

(10) Patent No.: US 8,308,711 B2
(45) Date of Patent: Nov. 13, 2012

(54) CATHETER SHAFT WITH A LUBRICIOUS SURFACE

(75) Inventors: Jeong S. Lee, Diamond Bar, CA (US);
Kenneth L. Wantink, Temecula, CA (US); Roseminda White, Wildomar, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1732 days.

(21) Appl. No.: 11/368,659

(22) Filed: Mar. 6, 2006

(65) Prior Publication Data
US 2007/0225746 A1   Sep. 27, 2007

(51) Int. Cl.
*A61M 25/00* (2006.01)

(52) U.S. Cl. .......... 604/523; 604/264; 604/266

(58) Field of Classification Search .......... 604/264, 604/266, 523
See application file for complete search history.

(56) References Cited

U.S. PATENT DOCUMENTS

| | | | |
|---|---|---|---|
| 4,820,466 A | | 4/1989 | Zachariades |
| 5,531,715 A | * | 7/1996 | Engelson et al. .......... 604/265 |
| 5,603,991 A | | 2/1997 | Kupiecki et al. |
| 5,843,032 A | * | 12/1998 | Kastenhofer .......... 604/103.06 |
| 6,190,358 B1 | | 2/2001 | Fitzmaurice et al. |
| 6,210,396 B1 | | 4/2001 | MacDonald et al. |
| 6,428,506 B1 | | 8/2002 | Simhambhatla et al. |
| 6,447,835 B1 | | 9/2002 | Wang et al. |
| 6,780,361 B1 | | 8/2004 | Sridharan et al. |
| 6,837,890 B1 | * | 1/2005 | Chludzinski et al. .......... 606/108 |
| 6,890,395 B2 | | 5/2005 | Simhambhatla |
| 6,960,187 B2 | | 11/2005 | Kastenhofer |
| 2003/0018353 A1 | | 1/2003 | Yang et al. |
| 2004/0122464 A1 | | 6/2004 | Wang et al. |
| 2004/0175558 A1 | | 9/2004 | El-Nounou et al. |
| 2006/0015168 A1 | | 1/2006 | Gunderson |

FOREIGN PATENT DOCUMENTS

| | | |
|---|---|---|
| EP | 1475120 A | 11/2004 |
| EP | 1475121 A | 11/2004 |
| WO | 0234165 A | 5/2002 |

OTHER PUBLICATIONS

Ticona Press Release "Ticona offers GUR and Hostalloy UHMW-PE products for injection molded parts needing toughness, abrasion resistance, and lubricity." Sep. 20, 2001.*
International Search Report, Dec. 4, 2007, pp. 1-4.
Bibliographic Data.

* cited by examiner

*Primary Examiner* — Laura Bouchelle
(74) *Attorney, Agent, or Firm* — Fulwider Patton LLP

(57) ABSTRACT

A catheter which has an elongated shaft having a layer of an ultra high molecular weight polyolefin, such as a melt-extruded ultra high molecular weight polyethylene (UHMWPE). The UHMWPE, forming at least in part a surface of the shaft, facilitates sliding a blood/contrast coated device along the shaft surface, and preferably substantially prevents or inhibits agglomerations of blood and contrast from adhering to the surface of the shaft in a patient's body lumen. In a presently preferred embodiment, the layer has a lubricious coating, such that the coated surface of the UHMWPE layer significantly decreases the force produced by the blood/contrast coated device sliding along the coated surface.

11 Claims, 3 Drawing Sheets

CATHETER SHAFT WITH A LUBRICIOUS SURFACE

FIELD OF THE INVENTION

This invention relates generally to catheters, and more particularly to intravascular catheters for percutaneous interventional procedures in a patient's vasculature.

BACKGROUND OF THE INVENTION

In percutaneous transluminal coronary angioplasty (PTCA) procedures a guiding catheter is advanced in the patient's vasculature until the distal tip of the guiding catheter is seated in the ostium of a desired coronary artery. A guidewire is advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter and the guidewire can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. See for example, U.S. Pat. No. 5,507,768 (Lau et al.) and U.S. Pat. No. 5,458,615 (Klemm et al.), which are incorporated herein by reference.

An essential step in effectively performing a PTCA or stent delivery procedure is properly positioning the balloon catheter at a desired location within the coronary artery, typically by sliding the catheter through a guiding catheter and over a guidewire within the patient's vasculature. In the design of catheter shafts, the trend has been towards minimizing the shaft diameter, to allow the shaft to be advanced further distally within the patient's vascular and to improve the shaft flexibility, resulting in a relatively small gap between the guidewire and the inner surface of the shaft. This relatively small gap exacerbates the problem of guidewire hang-up, i.e., an inability to freely slide the guidewire within the guidewire lumen, especially in a complex procedure or in a long procedure requiring many guidewire or catheter exchanges. Conventional intravascular catheters have commonly included an inner liner formed of a lubricious material such as Teflon or high density polyethylene (HDPE) to facilitate slidably advancing the catheter relative to the guidewire by reducing the frictional force of the guidewire against the inner surface of the shaft. However, one difficulty has been the tendency of small agglomerations of blood and contrast media within the guidewire lumen and adhering to the inner surface of the shaft, especially in complex or long procedures, making it difficult to advance or retract the catheter relative to a guidewire therein. Although anticoagulants such as heparin are commonly used to decrease the coagulation, it can be harmful to administer excessive amounts of anticoagulant during the sometimes lengthy procedure times required.

Accordingly, it would be a significant advance to provide a catheter with a relatively low profile shaft which nonetheless prevented or minimized guidewire hang-up, especially in a complex procedure or a long procedure requiring many guidewire or catheter exchanges. This invention satisfies these and other needs.

SUMMARY OF THE INVENTION

The invention is directed to a catheter which has an elongated shaft having a layer of an ultra high molecular weight polyolefin, such as a melt-extruded ultra high molecular weight polyethylene (UHMWPE). The UHMWPE, forming at least in part a surface of the shaft, facilitates sliding a blood/contrast coated device along the shaft surface, and preferably substantially prevents or inhibits agglomerations of blood and contrast from adhering to the surface of the shaft in a patient's body lumen. In a presently preferred embodiment, the layer has a lubricious coating, such that the coated surface of the UHMWPE layer significantly decreases the force produced by the blood/contrast coated device sliding along the coated surface.

The melt-extrudable UHMWPE is melt-extruded alone, or more typically with one or more additional layers of different polymeric material(s) to form a coextruded multilayered shaft of the invention. In contrast, more conventional non-melt-processible UHWMPE is typically formed into a desired shape using ram extrusion or otherwise molding a paste, slurry or pseudo-gel of the UHMWPE, and is joined to additional polymeric layers after that shaping process. Melt-extruding the UHMWPE inner layer together with additional layer(s) to form a coextruded multilayered tube facilitates the manufacturing procedure by avoiding the need for subsequent processing steps to combine with additional polymeric layer(s). The melt extruded UHMWPE is nonporous.

In a presently preferred embodiment, the UHMWPE layer forms an inner layer of the shaft. For example, in one embodiment the UHMWPE layer (or the coated UHMWPE layer) defines a guidewire lumen of a balloon catheter. A balloon catheter of the invention generally comprises an elongated catheter shaft having an inflation lumen, and a guidewire lumen configured to slidably receive a guidewire therein, and a balloon on a distal shaft section, which has an interior in fluid communication with the inflation lumen and which is configured to perform a procedure such as dilatation, stent delivery, occlusion, etc.

During intraluminal catheter procedures, the medical devices in the patient's blood vessel become coated with blood and contrast, which can severely impair the ability to slidably advance or retract the devices in the body lumen, especially as the blood coagulates around the device surfaces. For example, the surface of a guidewire positioned in the blood vessel (i.e., or in the guiding catheter within the blood vessel) will become coated with blood and/or contrast, so that the blood and contrast is introduced into the guidewire lumen of the catheter when the catheter is slid along the guidewire in the blood vessel. Agglomerations of blood and contrast within the guidewire lumen increase the force required to slide the guidewire therein by increasing the frictional resistance between the device surfaces and/or decreasing the guidewire clearance. However, the catheter shaft of the invention substantially prevents agglomerated blood and contrast within the guidewire lumen from significantly increasing the frictional force caused by the sliding movement of the catheter shaft relative to a guidewire in the shaft lumen, at least during the time periods common for typical interventional catheter procedures. As a result, the balloon catheter of the invention preferably prevents or limits guidewire hang-up in the guidewire lumen during the medical procedures.

The degree to which the catheter shaft surface becomes fouled with agglomerations of blood appears to depend on factors such as the nature of the material defining the catheter surface and the duration of the exposure to the blood. The time period required to produce a noticeable device/blood interaction and the frictional resistance generated therefrom are a measure of the extent to which the shaft provides the desired improved performance in a blood/contrast environment. In one test procedure, a blood/contrast coated guidewire within the catheter shaft lumen is slid relative thereto (i.e., the guidewire is longitudinally advanced and retracted over the stationary catheter shaft, or, more typically, the catheter is longitudinally displaced over the stationary guidewire), and the frictional resistance produced during multiple cycles is measured. The frictional resistance of the blood/contrast coated guidewire within, and sliding relative to, the catheter lumen is measured as a force (grams).

In a traditional test in which water is used instead of blood and contrast, the test does not account for the effect of the blood and contrast which would be present during an actual medical procedure in a patient's blood vessel. Thus, in water, the frictional force of the catheter on a guidewire depends mainly on the lubricity (coefficient of friction) of the sliding device surfaces (in addition to structural features such as the guidewire configuration, and clearance in the catheter lumen). In blood, the frictional force depends not just on the coefficient of friction of the surfaces of the catheter and guidewire but also on the degree of interaction with blood, potentially resulting in agglomerations of blood and contrast becoming adhered to the catheter shaft surface. Agglomerations of blood and contrast in the catheter lumen are preferably substantially prevented from adhering to the surface of a catheter of the invention, as reflected by a low frictional force required to slide a blood/contrast coated guidewire within and relative to the catheter shaft. The force required to slide the catheter of the invention over a guidewire in the presence of blood and contrast is believed to be low due to the nature of the inner surface of the shaft. Thus, the size of the shaft and the clearance of the guidewire therein can be optimized for other design considerations, and do not have to be sized in a particular manner in an attempt to provide for good guidewire movement during use.

In a presently preferred embodiment, the UHMWPE layer has a lubricious coating such as a silicone based coating, although at least in one embodiment the UHMWPE layer has a portion not covered by the lubricious coating. The uniformity of the lubricious coating along the length of the UHMWPE layer and the degree of coverage of the coating depends on a variety of factors such as the coating method and the concentration of the lubricious material applied to the UHMWPE layer surface. In one embodiment, the UHMWPE has portions not covered by the lubricious coating along the coated inner surface of the inner layer, so that the UHMWPE is partially exposed along the inner surface of the inner layer. As a result, the frictional force interaction with a blood/contrast coated guidewire is a function of both the lubricious coating and the nature of the underlying surface layer of the shaft (namely, the UHMWPE). The frictional force interaction of the catheter of the invention is preferably lower than that of a similar shaft which has the same lubricious coating but which replaces the UHMWPE with a different commonly used liner material such as high density polyethylene (HDPE).

The melt-extruded UHMWPEs have a weight average molecular weight of greater than about 1 million to about 10 million. The ultra high molecular weight polymers provide a low coefficient of friction that results in self-lubricating, non-stick surfaces after processing, and provide other advantages over lower molecular weight materials such as superior abrasion resistance and impact strength. In one embodiment, the melt-extruded UHMWPE has a dynamic coefficient of friction of about 0.10 to about 0.22 on dry polished steel surface. Unlike other lubricious materials such as fluoropolymers (e.g. PTFE), the UHMWPE materials are compatible with polyolefin based materials commonly used in catheter construction, and thus can be readily bonded thereto during catheter construction.

Suitable melt-extrudable UHMWPEs, commercially available from Ticona, are GUR®5113 and Hostalloy®731. GUR®5113 is a linear polyolefin resin with a weight average molecular weight of about 3 million g/mol, which, by way of comparison, is more than 10 times that of typical high molecular weight, high density polyethylene (HMW-HDPE) resins. Hostalloy® UHMWPE 731 is a linear polyolefin, melt-processible resin with a molecular weight exceeding most HMW-HDPE resins.

The term melt-processible should be understood to refer to polymers formulated to have good melt processibility, preferably to be melt-extrudable or injection moldable in a conventional screw extruder without requiring special extrusion equipment or conditions. The melt-processible UHMWPE has a relatively high mass melt flow rate which is preferably not less than about 5 to about 10 grams per ten minutes (as measured by the ISO 1133 Test Standard at 190° C./21.6 kg). The dilute solution viscosity of 0.0002 g/ml in decahydronaphthalene is about 200 to about 2000 mg/l. The density is 0.93~0.96 g/cm$^3$. The vicat softening point is approximately 80° C.

A method of making a catheter shaft of the invention, generally comprises melt extruding a melt-processible UHMWPE having a melt flow rate of not less than about 5 to about 10 g/10 minutes to form at least a layer of an extruded tube which forms at least a section of the shaft. In a presently preferred embodiment, a lubricious material is applied to the UHMWPE layer of the extruded tube.

A catheter of the invention provides an improved low friction shaft surface with reduced interaction with blood and contrast due to the ultra high molecular weight polyolefin (e.g., ultra high molecular weight polyethylene) layer of the shaft. In a preferred embodiment, the surface of the shaft of the invention does not seem to adhere to or frictionally engage a blood/contrast coated guidewire, as reflected by a low frictional force measurement. A melt-extrudable ultra high molecular weight polyolefin facilitates forming a multilayered shaft having the ultra high molecular weight polyolefin layer as an inner layer of the shaft, for improved device movement within the catheter lumen. The embodiment having a lubricious (e.g., silicone) coating on the ultra high molecular weight polyolefin layer has a significantly reduced frictional interaction with a blood/contrast coated guidewire, for improved ability to slidably position the catheter at a desired location with a patient's blood vessel. These and other advantages will become more apparent from the following Detailed Description and accompanying exemplary drawings.

DETAILED DESCRIPTION OF THE PREFERRED EMBODIMENTS

Figure 1:
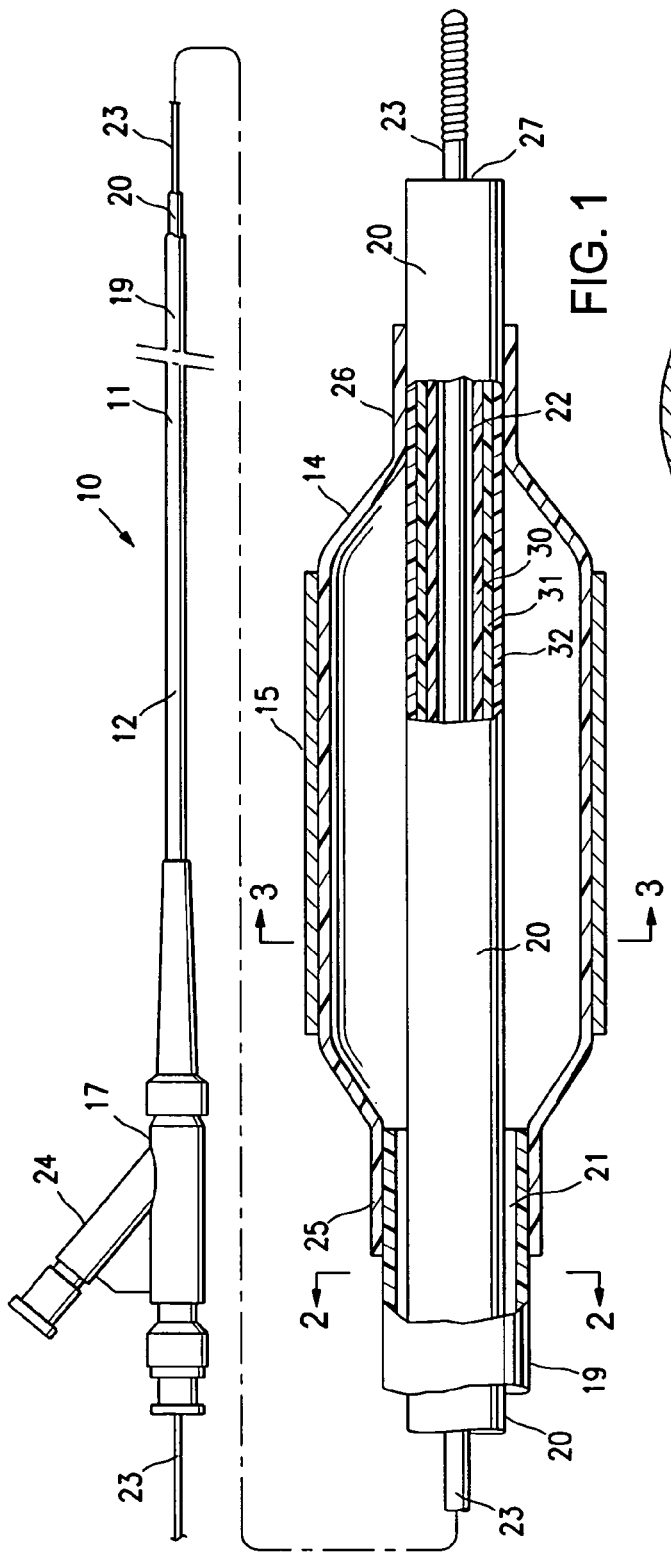
FIG. 1 is an elevational view, partially in section, of an over-the-wire type stent delivery balloon catheter embodying features of the invention.
Figure 2:
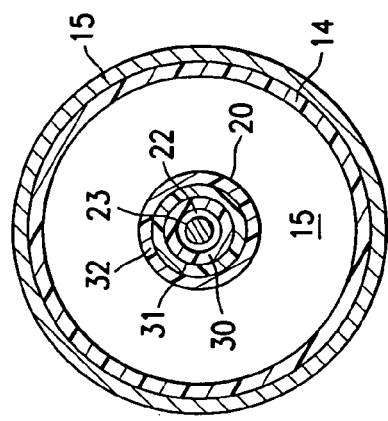
FIGS. 2-3 are transverse cross sectional views of the catheter of FIG. 1, taken along lines 2-2 and 3-3, respectively.
Figure 3:
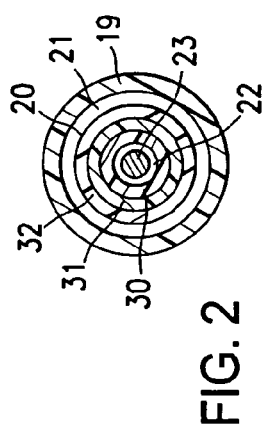

FIG. 1 illustrates an over-the-wire type stent delivery balloon catheter 10 embodying features of the invention, generally comprising an elongated catheter shaft 11 having a proximal shaft section 12, a distal shaft section 13, an inflation lumen 21, and a guidewire lumen 22 configured to slidably receive a guidewire 23 therein, and having a balloon 14 mounted on the distal shaft section. An adapter 17 on a proximal end of the catheter shaft provides access to the guidewire lumen 22, and has an arm 24 configured for connecting to a source of inflation fluid (not shown). A stent 15 is releasably mounted on the balloon for delivery and deployment within a patient's body lumen. The balloon catheter 10 is advanced in the body lumen with the balloon 14 in a low profile noninflated configuration with the stent 15 releasably mounted thereon, and the balloon inflated by introducing inflation fluid into the balloon interior to expand the balloon 14 and stent 15. The balloon 14 is then deflated to allow for repositioning or removal of the catheter in the body lumen, leaving the expanded stent 15 implanted in the patient's body lumen. FIG. 1 illustrates the balloon in an inflated configuration. FIGS. 2 and 3 illustrate transverse cross sectional view of the catheter of FIG. 1, taken along lines 2-2 and 3-3, respectively.

In the illustrated embodiment, the shaft 11 comprises an outer tubular member 19 defining the inflation lumen 21, and an inner tubular member 20 defining the guidewire lumen 22 and positioned in the outer tubular member 19 such that the inflation lumen 21 is the annular space between the inner surface of the outer tubular member 19 and the outer surface of the inner tubular member 20, as best shown in FIG. 2. The balloon 14 has a proximal skirt section 25 sealingly secured to the distal end of the outer tubular member 19, and a distal skirt section 26 sealingly secured to a distal end of the inner tubular member 20, so that an interior 15 of the balloon is in fluid communication with the inflation lumen 21 of the shaft. A variety of alternative suitable catheter shaft configurations can be used as are conventionally known. An atraumatic distal tip member is typically provided on the distal end of the inner tubular member, defining the distal-most end of the shaft. In the embodiment illustrated in FIG. 1, the guidewire lumen 22 extends to the proximal end of the catheter, from a guidewire distal port 27 at the catheter distal end to a guidewire proximal port at the proximal end of the shaft. In an alternative embodiment (not shown) in which the catheter is a rapid exchange type catheter, the guidewire lumen extends to a proximal guidewire port spaced distally from the proximal end of the catheter shaft.

The catheter shaft 11 is formed at least in part of a melt-extruded ultra high molecular weight polyolefin such as melt-processible UHMWPE. In a presently preferred embodiment, the melt-extruded UHMWPE forms an inner layer of the inner tubular member 20 of the catheter shaft 11. In the illustrated embodiment, the inner tubular member is a trilayer with a melt-extruded UHMWPE inner layer 30, middle layer 31, and outer layer 32. However, the melt-extruded UHMWPE can alternatively or additionally form other parts of the catheter shaft including outer layers such as an outer layer of the outer tubular member 19. Similarly, although illustrated as a trilayer, the inner tubular member 20 can have more or less than three layers in other embodiments. In a preferred embodiment, the three layers 30, 31, 32 all extend the full length of the inner tubular member 20. The inner tubular member 20 having an inner layer 30 of melt-extruded UHMWPE is preferably melt-coextruded using a conventional screw extruder, and then necked using conventional procedures to a smaller inner and outer diameter.

The middle and outer layers 31, 32 are preferably formed of a different material than the inner layer 30. For example, in a presently preferred embodiment the outer layer 32 is a polyamide such as a nylon or a polyether block amide (PEBAX), providing good bondability to the balloon 14. The polymeric material forming the outer layer 32 typically has a higher coefficient of friction than the UHMWPE of the inner layer 30. The middle layer 31 is typically a tie layer for bonding the inner layer 30 to the outer layer 32, such as a hot melt adhesive compatible with the UHMWPE, such as PRIMACOR (a functionalized polyolefin).

The melt-extruded UHMWPE preferably has a melt flow rate of at least about 5 to about 10 g/10 minutes, for good melt-processibility. For example, GUR®731 has a melt flow rate of about 10 g/10 minutes and is a presently preferred UHMWPE due to its superior melt-processibility which facilitates extruding the material to uniform desired dimensions.

In a presently preferred embodiment, the UHMWPE layer 30 has a lubricious coating (not shown) on the inner surface of the inner layer 30. The coating is typically applied by a drawing or forcing a solution through the lumen 22 to coat substantially the entire length of the inner layer 30. However, alternative methods can be used to apply the lubricious coating.

The lubricious coating is preferably a silicone material, and most preferably a hydrophobic silicone mixture of a moisture-cured aminofunctional dimethylsiloxane copolymer and a non-curing polydimethylsiloxane (PDMS), which significantly reduces the frictional force of the blood/contrast coated guidewire within the shaft lumen. For example, a mixture of DOW Corning MDX 4159 (medical grade dispersion of an aminofunctional dimethylsiloxane copolymer) and DOW Corning 360 (medical grade PDMS) in solvent such as heptane and isopropanol, applied to the inner surface of layer 30, is dried at about 70-100° C. for about 5 to 72 hours in a humidified environment of about 25 to about 75% humidity to form the lubricious coating. Alternatively, sterilization in ethylene oxide/steam accomplishes a similar outcome. The concentration of the mixture of the MDX 4159 and 360 siloxanes is about 0.5 to about 30%, and a variety of suitable solvents can be used including toluene, THF, and ethanol. Factors such as the concentration of the mixture affect the resulting coating, particularly during coating of an inner surface of the shaft, such that the shaft can have a uniform or nonuniform coverage and coating thickness along the length of the shaft.

During use, the catheter 10 is advanced within a patient's blood vessel, causing the blood therein to be introduced into the catheter's guidewire lumen 22. Similarly, a large amount of viscose contrast is typically introduced through the guidewire lumen 22 to aid in visualization of the device(s) in the blood vessel under fluoroscopy. Commonly used contrast includes ionic and nonionic contrasts such as Visipaque, Omnipaque, and Hexabrix. However, the force required to slide the catheter 10 over a guidewire in the presence of blood and contrast is low due to the nature of the inner surface of the inner tubular member 20, at least during the time periods common for typical interventional catheter procedures. For a typical stent delivery procedure, the catheter is in the blood vessel for about 5 to about 30 minutes.

The following Examples demonstrate the improved performance provided by a catheter shaft of the invention. Examples 1 and 2, and Comparative Examples 3 and 4 all involve trilayer extruded tubular members having dimensions suitable for use as an inner tubular member of a balloon catheter, such as inner tubular member 20 of balloon catheter 10 of FIG. 1. Examples 1 and 2 have a melt-processible UHMWPE inner layer in accordance with the invention, whereas Comparative Examples 3 and 4 have an HDPE inner layer.

Figure 4:
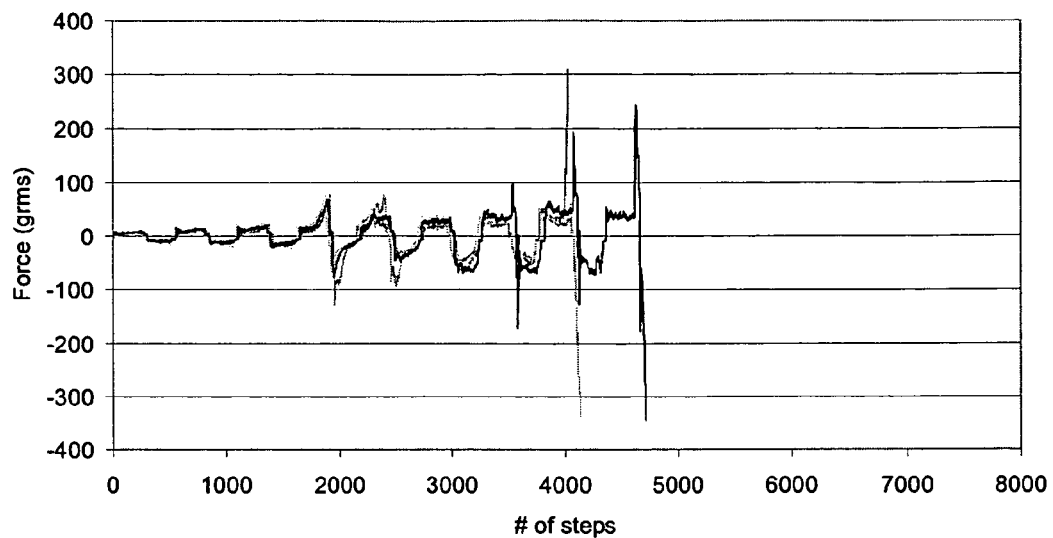
FIGS. 4 and 5 are graphical frictional force data for multiple cycles of catheter shafts of the invention sliding over a guidewire in the presence of blood and contrast.

Example 1 (FIG. 4). Trilayer tubular members having an outer layer of PEBAX, a middle layer of PRIMACOR, and an inner layer of Hostalloy®731 UHMWPE were melt extruded using a conventional screw extruder, with an inner diameter (ID) of about 0.45 mm and an outer diameter (OD) of about 0.60 mm, and the tubing is then necked to an ID of 0.445 mm and an OD of about 0.584 mm at 120° F. and stabilized at 212° F. for 10 minutes.

Figure 5:
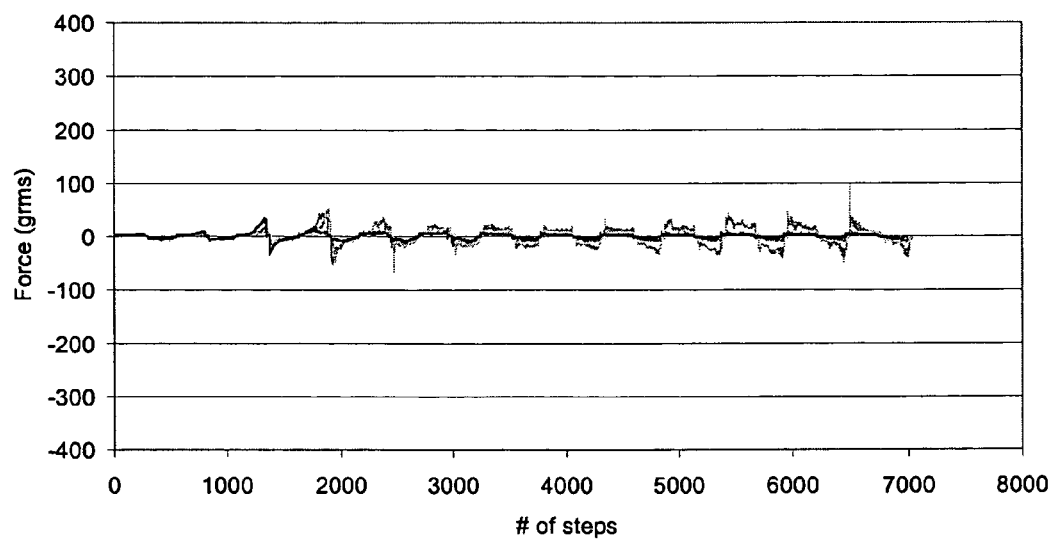

Example 2 (FIG. 5). The trilayer tubular members of Example 1 were coated with a silicone-based coating by drawing a mixture of DOW Corning MDX 4159 and DOW Corning 360 in solvent through the lumen of the trilayer tubular members, and were sterilized using EtO and steam.

Figure 6:
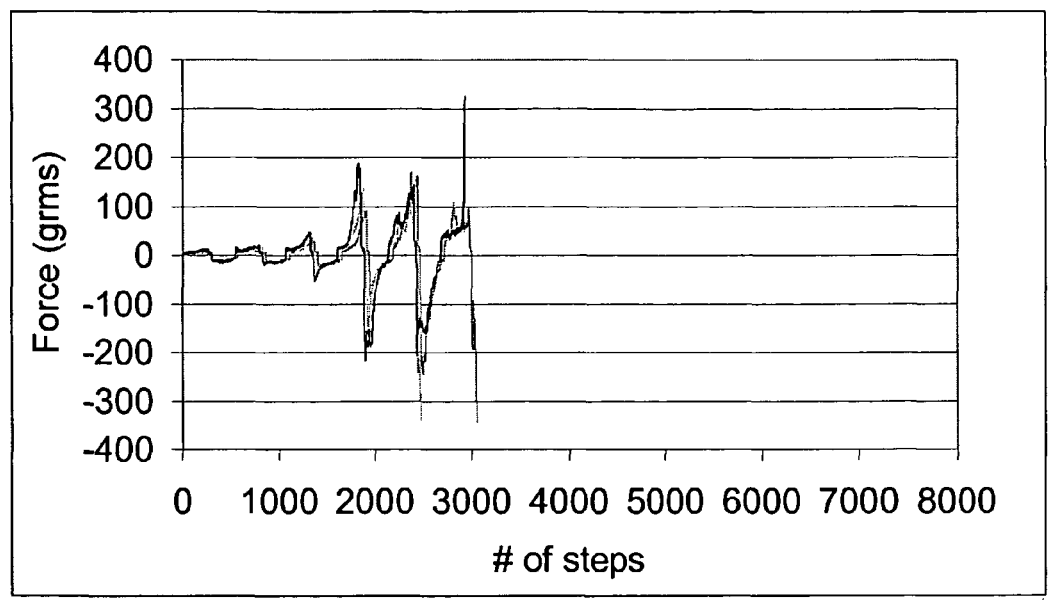
FIGS. 6 and 7 are graphical frictional force data for multiple cycles of comparison catheter shafts sliding over a guidewire in the presence of blood and contrast.

Comparative Example 3 (FIG. 6). A trilayer tubular member having an outer layer of PEBAX 7233, a middle layer of PRIMACOR adhesive polymer, and an inner layer of HDPE (specifically, LM 6007-00 from Equistar, a Lyondell Company) were melt extruded using a conventional screw extruder, with a tapering diameter which was no smaller than the smallest diameter of the tubular members of Examples 1 and 2, and specifically with an extruded proximal ID of about 0.483 mm and OD of about 0.635 mm, to a distal ID of about 0.445 mm and OD of about 0.584 mm.

Figure 7:
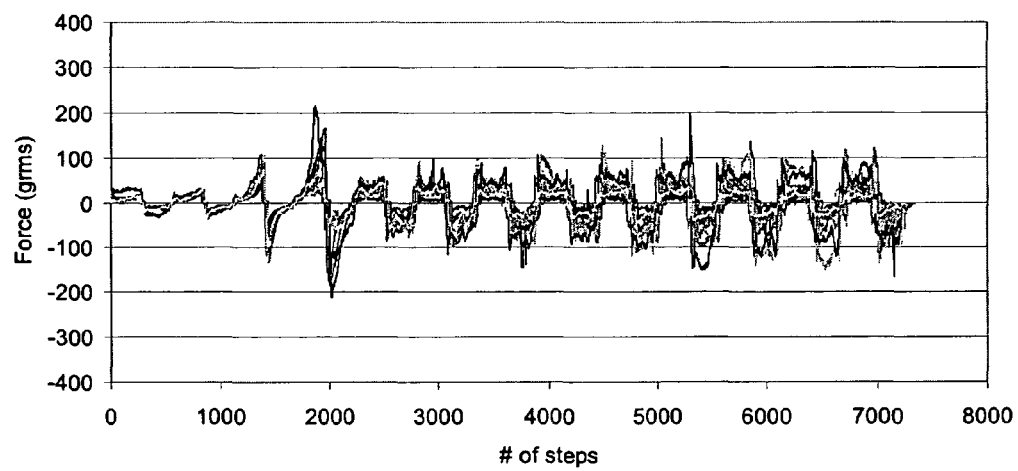

Comparative Example 4 (FIG. 7). The trilayer tubular members of Comparative Example 3 were coated with a silicone-based coating by drawing a mixture of DOW Corning MDX 4159 and DOW Corning 360 in solvent through the lumen of the trilayer tubular members, and were sterilized using EtO and steam.

The frictional resistance of a blood/contrast coated guidewire in the trilayer tubular members of Examples 1-4 was measured, and the results are shown in FIGS. 4-7, respectively. Specifically, the tubular member is slid onto the proximal end of a guidewire within a fixture which holds the tubular member and guidewire therein in a straight (not bending) condition. The distal section of the guidewire is coated with a 1:2 sheep blood: non-ionic type contrast (Visipaque) mixture, and the tubular member is advanced and retracted a given distance longitudinally along a blood and contrast coated portion of the guidewire while a transducer on the guidewire measures and records the force (i.e., frictional resistance) to the movement of the guidewire within the tubular member lumen. The resulting force measurement (in grams) has a positive or negative value depending on whether the catheter is being advanced or retracted along the guidewire. A test comprises a series of advancements and retractions, which make up 6.5 cycles (13 total series of advancements or retractions) or less than 6.5 cycles if significant resistance is produced. Multiple samples were tested for each example, so that the results of the different samples for a given example are indicated in varying shades of grey on each graph.

During each cycle of advancement and subsequent retraction, the catheter is moved the same distance along the guidewire, and that distance is represented as a Step value in FIGS. 4-7, with each series being about 550 steps. The distance is chosen to be a significant percentage of the length of the tubular member, and more particularly to approximate the typical length of the portion of the guidewire lumen which becomes positioned within the patient's distal tortuous vasculature during use. The tubular members in Examples 1-4 each had a length of about 65 cm and the movement distance of each series was about 45 cm. The same type of guidewire was used in each test, namely a Guidant ACS 0.014 inch BMW guidewire.

The graphs of FIGS. 4-7 illustrate the time period required to produce a noticeable device/blood interaction and the frictional resistance generated therefrom. The tubular members of Example 2, having the silicone coated UHMWPE inner layer, performed significantly better than the tubular members of Examples 1, 3 and 4, with a very low overall force value which increased only a relatively small amount over the duration of the test (see FIG. 5). Specifically, the force is never greater than about 100 grams (i.e., 100 grams or −100 grams), and is typically significantly less than 100 grams, and more specifically less than about 50 grams. Significantly, the tubular members of Example 2 had a lower force value than the tubular members of Example 4, despite having the same silicone-based coating. Thus, the nature of the UHMWPE material appears to play a role in avoiding the interaction between the catheter shaft and the blood and contrast, thereby providing improved low frictional resistance to a sliding blood/contrast coated guidewire. Additionally, the tubular members of Example 1, having a noncoated UHMWPE inner layer, had a lower force value and a longer delay before any noticeable increase in the force was observed during the test when compared with the corresponding comparative example, namely the tubular member of Comparative Example 3 having a noncoated HDPE inner layer.

In SEM (scanning electron microscope) images of the inner surface of tubular members of Examples 1-4, the surface appears to have raised ridges between valleys of an irregular surface, with the lubricious coating partially filling these valleys in the coated tubular members of Examples 2 and 4. Thus, one embodiment comprises a coated UHMWPE layer, in which the raised ridges are more thinly coated than the valleys of the UHMWPE irregular surface, or are in part not coated at all with the lubricious coating.

Thus, a catheter shaft embodying features of the invention which has an UHMWPE layer forming at least in part a surface of the shaft, preferably allows a blood/contrast coated device to slide therealong with a low resistance force, and preferably with agglomerations of blood and contrast fluid substantially prevented from adhering to the surface of the shaft in a patient's body lumen.

The dimensions of catheter 10 are determined largely by the size of the balloon and guidewire to be employed, the catheter type, and the size of the artery or other body lumen through which the catheter must pass or the size of the stent being delivered. Typically, the outer tubular member 19 has an outer diameter of about 0.025 to about 0.04 inch (0.064 to 0.10 cm), usually about 0.037 inch (0.094 cm), and the wall thickness of the outer tubular member 19 can vary from about 0.002 to about 0.008 inch (0.0051 to 0.02 cm), typically about 0.003 to 0.005 inch (0.0076 to 0.013 cm). The inner tubular member 20 typically has an inner diameter of about 0.01 to about 0.018 inch (0.025 to 0.046 cm), usually about 0.016 inch (0.04 cm), and a wall thickness of about 0.004 to about 0.008 inch (0.01 to 0.02 cm). The overall length of the catheter 10 may range from about 100 to about 150 cm, and is typically about 143 cm. Preferably, balloon 14 has a length about 0.8 cm to about 6 cm, and an inflated working diameter of about 2 mm to about 10 mm.

The various catheter components may be joined using conventional bonding methods such as by fusion bonding or use of adhesives. Although the shaft is illustrated as having an inner and outer tubular member, a variety of suitable shaft configurations may be used including a dual lumen extruded shaft having a side-by-side lumens extruded therein. Additionally, although the embodiment illustrated in FIG. 1 is an over-the-wire type balloon catheter, the catheter of this invention may comprise a variety of intravascular catheters, including rapid exchange type balloon catheters, and a guiding catheter having a device lumen configured for delivering catheters or other devices.

While the present invention is described herein in terms of certain preferred embodiments, those skilled in the art will recognize that various modifications and improvements may be made to the invention without departing from the scope thereof. Although discussed primarily in terms of an elongated shaft of a catheter formed at least in part of melt-extruded UHMWPE, the melt-extruded UHMWPE could alternatively be used to form a variety of medical devices and components thereof, particularly melt extruded tubular components including an outer surface layer of a guidewire. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. A catheter, comprising an elongated shaft having a proximal end, a distal end, a lumen extending to a port in a distal shaft section, and a non-porous inner layer of melt-extrudable ultra high molecular weight polyolefin having a mass melt flow rate of at least about 5 to 10 g/10 minutes at 190 C. and 21.6 kg load, wherein such inner layer is coated with a lubricious coating.

2. The catheter of claim 1 wherein the melt-extrudable ultra high molecular weight polyolefin is a non-porous melt-extrudable ultra high molecular weight polyethylene.

3. The catheter of claim 2 wherein the shaft is multilayered and wherein said inner layer has a lower coefficient of friction than other layers.

4. The catheter of claim 3 wherein the lumen defined by the coated inner surface of the inner layer is a device delivery lumen of a guide catheter or a guidewire lumen of a balloon catheter.

5. The catheter of claim 1 wherein the lubricious coating is a hydrophobic silicone polymeric material.

6. The catheter of claim 5 wherein the hydrophobic silicone polymeric material is a mixture of an aminofunctional dimethylsiloxane copolymer and a polydimethylsiloxane.

7. A balloon catheter, comprising:
    a) an elongated shaft having an outer tubular member with an inflation lumen extending therein, and an inner tubular member disposed within at least a section of the inflation lumen and with a guidewire lumen extending therein, the inner tubular member having an inner surface layer coextruded with an outer surface layer, the inner layer being a melt-extrudable nonporous ultra high molecular weight polyethylene and having a lubricious coating of a hydrophobic silicone polymeric material on an inner surface of the inner layer, such that agglomerations of blood and contrast fluid within the guidewire lumen are substantially prevented from adhering to the coated inner surface of the inner layer of the shaft in a patient's body lumen; and
    b) a balloon on a distal shaft section having an interior in fluid communication with the inflation lumen.

8. The balloon catheter of claim 7 wherein the ultra high molecular weight polyethylene has a relatively lubricious surface with a lower coefficient of friction than the outer layer.

9. The balloon catheter of claim 7 wherein the hydrophobic silicone polymeric material is a mixture of a moisture-cured aminofunctional dimethylsiloxane copolymer and a non-curing polydimethylsiloxane.

10. The balloon catheter of claim 7 wherein the inner surface of the ultra high molecular weight polyethylene layer has a portion not covered by the lubricious material coating.

11. The balloon catheter of claim 7 wherein the inner surface of the ultra high molecular weight polyethylene inner layer has an irregular surface with peaks which are not covered by the lubricious material and which are between valleys covered by the lubricious material, so that the ultra high molecular weight polyethylene is partially exposed along the coated inner surface of the inner layer.

* * * * *